US00PP12516P2

(12) United States Plant Patent
Noodelijk

(10) Patent No.: US PP12,516 P2
(45) Date of Patent: Apr. 2, 2002

(54) CHRYSANTHEMUM PLANT NAMED 'REGGIE DARK PINK'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/561,930

(22) Filed: May 1, 2000

(51) Int. Cl.[7] ..... A01H 5/00
(52) U.S. Cl. ..... Plt./297
(58) Field of Search ..... Plt./297

(56) References Cited

PUBLICATIONS

UPOV–ROM GTITM Computer Database, 2001/01, GTI Jouve Retrieval Software, citation for 'Reggie Dark Pink'.*

* cited by examiner

*Primary Examiner*—Bruce R. Campell
*Assistant Examiner*—Susan B. McCormick
(74) *Attorney, Agent, or Firm*—Parkhurst & Wendel, L.L.P.

(57) ABSTRACT

A Chrysanthemum plant named 'REGGIE DARK PINK' characterized by its small sized blooms with purple ray-florets and purple disc florets.

2 Drawing Sheets

RELATED CULTIVARS

'REGGIE DARK PINK' is related to 'REGGIE' (U.S. plant patent application Ser. No. 09/561,931) and 'REGGIE YELLOW' (U.S. plant patent application Ser. No. 09/562, 138). 'REGGIE DARK PINK' and 'REGGIE YELLOW' are both color mutants of 'REGGIE'.

BACKGROUND OF THE INVENTION

'REGGIE DARK PINK' is a product of a breeding and selection program which had the objective of finding color mutants of 'REGGIE'. The new plant of the present invention comprises a new and distinct cultivar of chrysanthemum plant that is a natural occuring sport of a parent chrysanthemum named 'REGGIE'. A comparison with Parent chrysanthemum 'REGGIE' is also made in this application. The new cultivar was discovered as a whole plant mutation in May 1995 by Rob Noodelijk in a controlled environment (greenhouse) in Rijsenhout Holland. The first act of asexual reproduction of 'REGGIE DARK PINK' was accomplished when vegetative cuttings were taken from the initial selection in July 1995 in Rijsenhout Holland.

SUMMARY OF THE INVENTION

The present invention is a new and distinct variety of chrysanthemum bearing small sized blooms with purple ray-florets and purple disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
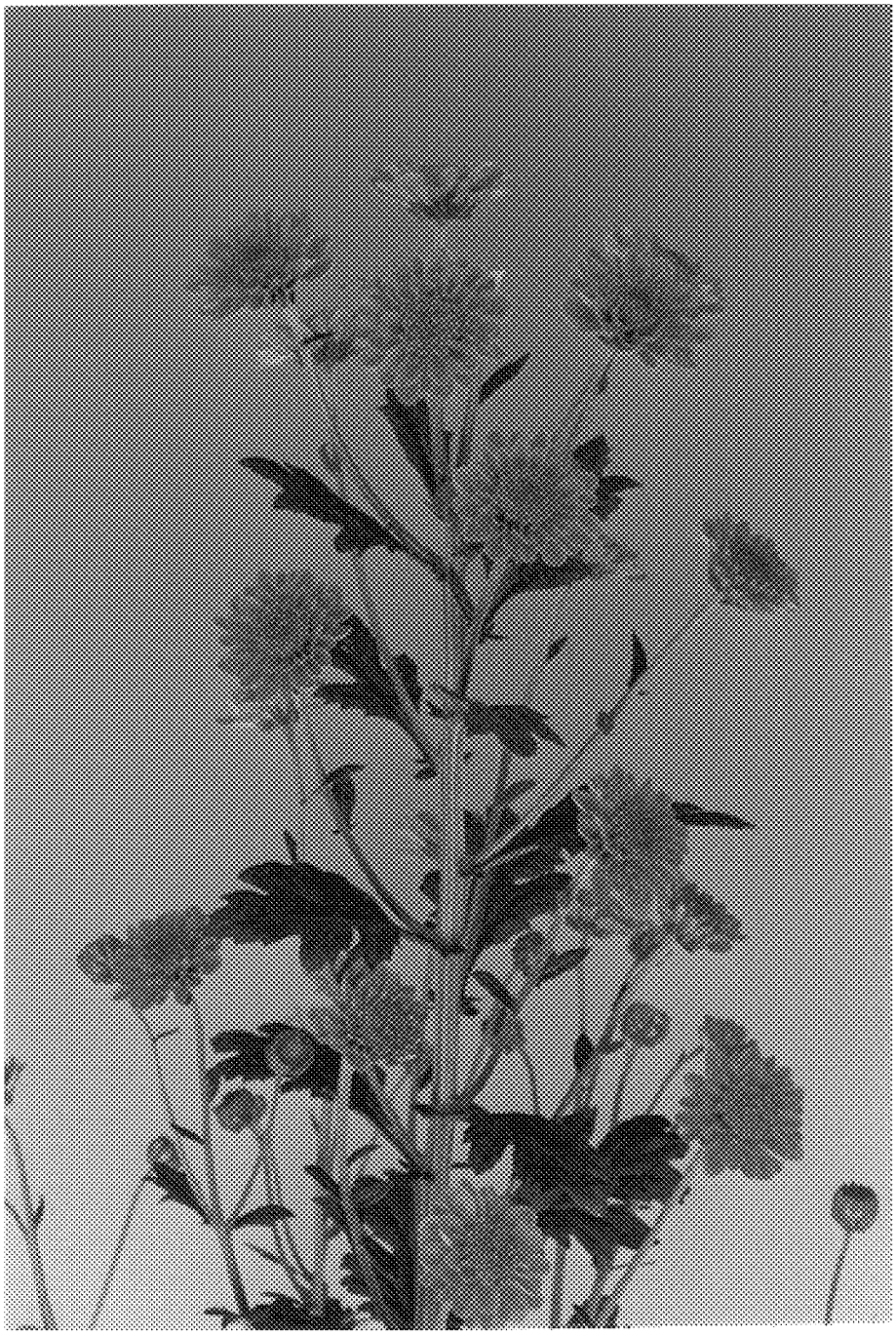
FIG. 1 shows a plant of the cultivar in full bloom.
Figure 2:
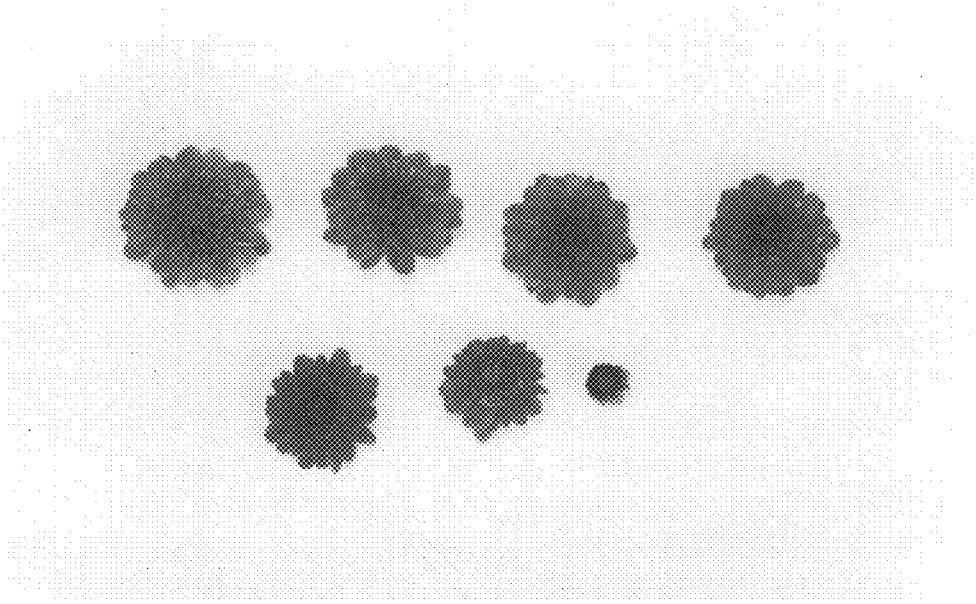
FIG. 2 shows the various stages of bloom of the new cultivar.
Figure 3:
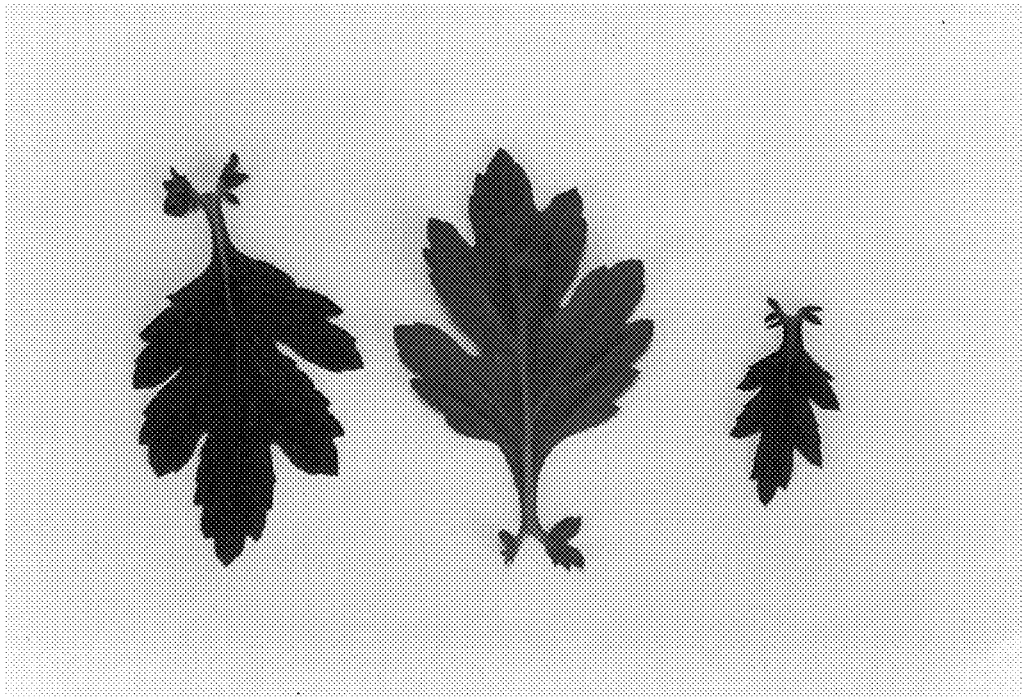
FIG. 3 shows the various stages of foliage and petiole of the new cultivar.

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 47 days after an average of eight long days. After this long day period to flowering growth retardants were applied 2 times in an average dose of 2.5 gram/liter water. No tests were done on disease or insect resistance or susceptibility. This new variety produces small sized blooms with purple ray-florets and purple disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'REGGIE DARK PINK' can be planted without assimilation lighting (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to 'REGGIE DARK PINK' is 'REGGIE' and 'REGGIE YELLOW'. When REGGIE, 'REGGIE DARK PINK' and 'REGGIE YELLOW' are being compared the following differences and similarities are noticed: The difference of 'REGGIE', 'REGGIE DARK PINK' and 'REGGIE YELLOW' is the ray-floret color for which characteristics 'REGGIE DARK PINK' has been selected out of REGGIE. 'REGGIE DARK PINK' is dark pink, 'REGGIE YELLOW' is yellow and 'REGGIE' is white. All other characteristics of 'REGGIE' and 'REGGIE DARK PINK' are similar.

The following is a description of the plant and characteristics that distinguish 'REGGIE DARK PINK' as a new and distinct variety. The color designations are taken from the plant itself. Accordingly, any discrepancies between the color designations and the colors depicted in the photographs are due to photographic tolerances. The color chart used in this description is: The Royal Horticultural Society Color Chart, Edition 1995.

Botanical Description of CULTIVAR 'REGGIE DARK PINK'

Bud:
- *Size*.—Small Cross-section 1.0 cm height 0.6 cm.
- *Shape*.—Round and flat.
- *Outside color*.—Red-purple 70 A.
- *Involucral bracts*.—2 rows, length 7 mm, width 3 mm.
- *Involucral bracts among disc-florets*.—Not present.
- *Involucral bracts color*.—Yellow-green 144 A.

Bloom:
- *Type*.—Anemone.
- *Height*.—Flat.
- *Size*.—Small.
- *Fully expanded*.—3.0–4.0 cm.
- *Number of blooms per stem*.—Approx. 16 blooms per stem.
- *Performance on the plant*.—5 weeks.
- *Seeds*.—Not produced.
- *Fragrance*.—Typical chrysanthemum.

Color:
- *Center of the flower* (*disc-florets*).—Immature Red-purple 70 A with green 138 A in the center. Mature completely Red-purple 70 A.
- *Color of upper surface of the ray-florets*.—Red- purple 70 A.
- *Color of the lower surface of the ray-florets*.—Red-purple 70 B.
- *Tonality from distance*.—A spray mum with purple flowers and a purple cushion center.
- *Discoloration to color*.—Red-purple 70 B.

Ray florets:
- *Texture*.—Upper and under side smooth.
- *Number*.—32–36 (2 rows).
- *Cross-section*.—Concave.
- *Longitudinal axis of majority*.—Incurving.
- *Length of corolla tube*.—Very short.
- *Ray-floret margin*.—Entire.
- *Ray-floret length*.—1.8–2.0 cm.
- *Ray-floret width*.—0.7–0.9 cm.
- *Ratio length/width*.—Low.
- *Shape of tip*.—Rounded.

Disc florets:
- *Disc diameter*.—1.2–1.4 cm.
- *Distribution of disc florets*.—Numerous clearly visible at all stages of flowering.
- *Shape*.—Petaloid.
- *Color*.—Red-purple 70 A, greyed-red 178 B at the tip.
- *Receptacle shape*.—Domed raised.

Reproductive organs:
- *Stamen* (*present in disc florets only*).—Yellow-green, thin 4 mm. in length.
- *Number of stamen*.—Grown together as one.
- *Stamen color*.—Yellow-green 144 B.
- *Pollen*.—None.
- *Pollen color*.—Not applicable.
- *Styles* (*present in both ray and disc florets*).—Yellow-green, thin.
- *Style color*.—Yellow-green 144 B.
- *Style length*.—5 mm.
- *Stigmas*.—Yellow-green.
- *Stigma width*.—2 mm.
- *Ovaries*.—Enclosed in calyx.

Plant:
- *Form*.—A spraymum meant for use as a cut flower.
- *Growth habit*.—Upright.
- *Growth rate*.—Moderate.
- *Height*.—100–105 cm.
- *Internodes*.—2.0–2.5 cm.
- *Spray formation*.—Pyramidal to cylindrical.
- *Stem color*.—Yellow-green 144 A.
- *Stem strength*.—Medium.
- *Stem brittleness*.—Present.
- *Stem anthocyanin coloration*.—Present, with a slight layer of greyed-red.
- *Peduncle length*.—Near the top 10 cm., near the middle 14 cm., near the bottom 18 cm.
- *Peduncle color*.—Yellow-green 144 A.
- *Flowering response* (*photo-periodic controlled crop, not natural season*).—47 days.

Foliage:
- *Color*.—Upper side green 137 A under side 137 B.
- *Size*.—Medium; length 6.5 cm, width 5.5 cm.
- *Quantity* (*number per lateral branch*).—28–32.
- *Shape*.—Ovate.
- *Texture upper side*.—Glabrous.
- *Texture under side*.—Pubescent.
- *Venation arragement*.—Palmate.
- *Shape of the margin*.—Serrated.
- *Shape of base of sinus between lateral lobes*.—Round.
- *Margin of sinus between lateral lobes*.—Converging.
- *Shape of base*.—Truncate sometimes asymmetric.
- *Apex*.—Mucronate.

Differences with the comparison varieties

| | 'REGGIE PINK' | DARK 'REGGIE' | 'REGGIE YELLOW' |
|---|---|---|---|
| Ray-floret color | Red-purple A | 70 White 155 D | Yellow 13 B |

I claim:

1. A new and distinct variety of chrysanthemum plant as described and illustrated.

* * * * *